United States Patent [19]

Clifford et al.

[11] Patent Number: 4,593,284
[45] Date of Patent: Jun. 3, 1986

[54] ANALOG AND DIGITAL SIGNAL TRANSMITTER

[75] Inventors: Mark J. Clifford, New Brighton; Robert H. Hock, Brooklyn Center; Douglas M. Jagunich, Minneapolis; Paul J. Robinson, St. Paul, all of Minn.

[73] Assignee: Medtronic, Inc., Minneapolis, Minn.

[21] Appl. No.: 589,441

[22] Filed: Mar. 14, 1984

[51] Int. Cl.[4] .............................................. G08C 19/02
[52] U.S. Cl. ................................ 340/870.18; 128/904
[58] Field of Search ..................... 340/870.18, 870.07, 340/870.12, 870.26, 825.58; 128/680, 689, 903, 904

[56] References Cited

U.S. PATENT DOCUMENTS 3,426,150  2/1969  Tygart ........................ 340/870.18 X

OTHER PUBLICATIONS

Vrincianu, R., Electro-Rheocardiotelemetric ... Contraction, International Symposium on Biotelemetry, Netherlands, May '71, pp. 196-201.

Primary Examiner—Jerry W. Myracle
Attorney, Agent, or Firm—Reed A. Duthler; Joseph F. Breimayer; John L. Rooney

[57] ABSTRACT

Real time analog and digital information are simultaneously transmitted from a transmitter circuit. In the disclosed embodiment, the analog signals are obtained from ECG apparatus and the digital signals are derived by a process or from analysis of the ECG signals. The system is implemented by summing the output signals from the FM oscillator and the FSK oscillator in an amplitude summing amplifier and transmitting the result in combined waveform, preferably over a phone line, although radio transmission may alternately be used as well as other types of transmission of the resulting signal.

In the present invention, the analog signal is employed to frequency modulate a frequency modulated oscillator, and the digital information signal is used to obtain frequency shift keying of a FSK oscillator. In the disclosed embodiment, the frequency modulated oscillator and the FSK oscillator have frequencies that are within the band pass of the telephone line and, of course, have sufficient separation so that the resulting output signal may be filtered and decoded to obtain the separate analog and digital components. After the FM modulated analog information signal and the digital controlled FSK signals are obtained, they are coupled to an amplitude summing amplifier which provides a single amplitude summation of the two signals as applied to the modem and thus over the phone line. In this manner, the simultaneous transmission of both analog and digital information is provided in efficient but effective system.

4 Claims, 1 Drawing Figure

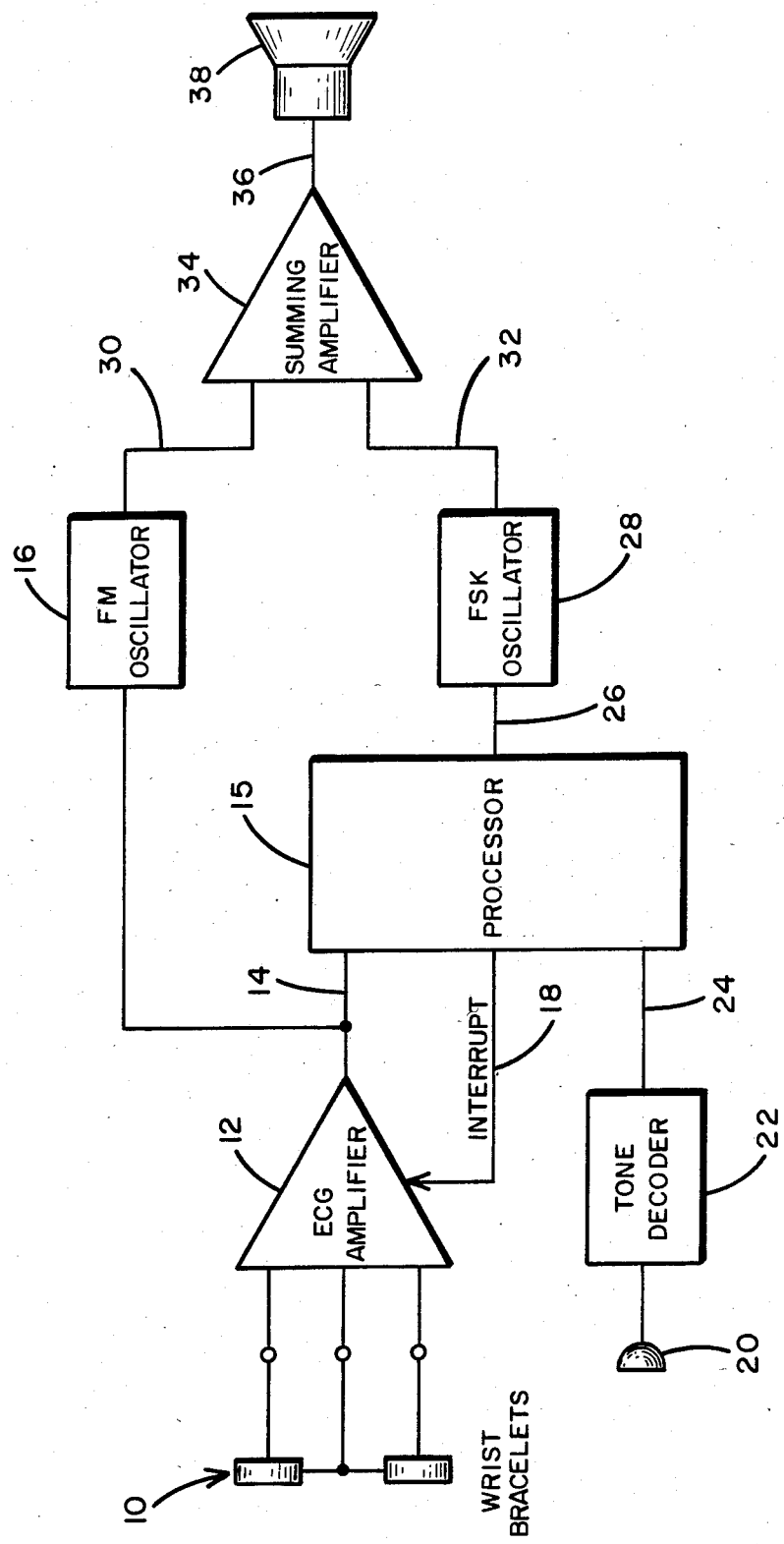

ANALOG AND DIGITAL SIGNAL TRANSMITTER

BRIEF DESCRIPTION OF THE DRAWINGS

The present invention is described by reference to the drawing which shows a block diagram of an embodiment as intended for use with an ECG analog pickup and transmission over telephone lines.

TECHNICAL DESCRIPTION OF THE INVENTION

The present invention is disclosed by reference to a monitoring system for monitoring a patient with an artificial implanted pulse generator in which a modem is used to transmit information to a remote location. The general principles of the present invention, however, are applicable for analysis and transmission of other types of analog information by other types of transmission media.

In the disclosed embodiment, the wrist electrodes 10 are applied to the patient to pick up an ECG signal which is sent to an ECG amplifier 12. The output of the ECG amplifier 12 is sent to a processor 15 which is utilized to analyze incoming analog signals to determine such things as rate, pulse and/or pulse width and the time of occurrence of the various PQRS and T portions of patient's natural heart beat as well as artifacts dealing with artificial pulse stimulation. The ECG signal is also coupled to frequency modulate an FM oscillator 16. For the telephone application of a disclosed embodiment, the nominal frequency of the oscillator 16 may be 1500 Hz with a modulation range of ±500 Hz. The processor 15, after receiving the incoming information from the amplifier 12, may utilize it to provide an interrupt signal on the line 18 to the ECG amplifier. This interrupt signal may be used when the device is employed with receivers that do not have a capability of decoding digital processed signals by the processor 16. In this instance the interrupt signal on the line 18 may be utilized to control the amplifier 12 so that information such as the pulse width of a pacing pulse may be measured and this information may be transmitted through the FM oscillator 16 by utilizing a fixed frequency, or tone, which has a width that is a predetermined multiple of the measured pulse width that was detected. The system of the FIGURE is linked to the telephone through a microphone or receiving section 20 which is coupled to a tone decoder 22. When a tone of the proper frequency is supplied to the tone decoder, for example a signal in the range of 800-1000 Hz, the tone decoder 22 will produce a logic level signal on the output line 24 which indicates that a remote receiver/transmitter is linked to the transmitter/receiver of the FIGURE.

The portion of the transmitter of the FIGURE that has been thus far described corresponds generally to similar components in prior transmitters, particularly those used to transmit the ECG to a remote location. One particular such transmitter is one made by Medtronic, Inc. under the Model No. 9408. It is becoming increasingly desirable, however, to be able to transmit information relating to the occurrence of these particular events, such as an atrial sense event, a ventricular sense event, a ventricular pace event, etc. This type of information called micropulses is transmitted digitally from a most advanced implantable pulse generator. An example of the manner in which such transmission is provided from an implantable pulse generator is disclosed in U.S. Pat. No. 4,281,664 to Duggan. The present invention incorporates a means whereby the transmission of both marker and analog information may be achieved over telephone lines, or alternately via a long distance transmission system, whereas the system disclosed in the Duggan patent is suitable only for a short distance transmission, for example, between an implantable pulse generator and a relatively closely positioned programming head of a programming device.

The processor 15 after analyzing the incoming information signal may supply digital output signals on the line 26. The digital output signals may also be derived from a separate input device, which may be either analog or digital for the measurement of blood pressure, blood oxygen, respiration, or other physiological or other type of information. Digital signals on the line 26 are supplied to frequency-shift key oscillator 28 (FSK). The FSK oscillator operates over a band width which is sufficiently removed from the frequency of the FM oscillator 16 so that through filtration and selection the two signals may be seperated at the receiving end. When the logic signal on the line 26 is at one logic level the output frequency of the FSK oscillator on the line 32 may, for example, be at 2600 Hz, and when the signal on the line 26 is at the other logic level, the output frequency may be at 2900 Hz on the line 32. Output of the FM oscillator is supplied on the line 30 and the output of the FSK oscillator is supplied on the line 32 to separate inputs of the amplitude summing amplifier 34. The amplifier 34 provides an amplitude summation of the signals on the line 30 and 32 and provides a summed signal on the line 36 to an output transmitter, or speaker on the prefered embodiment to the transmitting section of a conventional telephone which is coupled to a modem for transmission over telephone lines.

While the present invention has been described by reference to a particular embodiment in which analog information is obtained from an ECG reading and the output signal is transmitted on telephone lines, the scope of the invention is not limited to such embodiment in that it is intended to emcompass the amplitude summation of an FM modulated signal containing analog information and a frequency shift keying signal containing digital information in general terms.

What is claimed is:

1. A transmitter for transmitting information derived from both analog and digital sources comprising analog signal input means, frequency modulated oscillator means modulated by said analog signal input means, digital signal input means, frequency shift keying oscillator means constructed to operate at a first frequency when said digital input signal means is supplying a digital signal at a first logic level and to operate at a second output frequency when said digital signal input means is at a second output logic level, and an amplitude output summing amplifier for summing together the output of said frequency modulated oscillator means and said frequency shift keying oscillator means.

2. A system as provided in claim 1 wherein said system comprises a processor coupled to receive said analog input signal from said analog signal input means, to analyze said signal and to provide a digital output signal to said frequency shift keying oscillator representative of its analysis.

3. A system as claimed in claim 1 wherein said analog input signal means is derived from sensing means which senses physiological signals of a patient.

4. A system as claimed in claim 3 wherein said summing amplifier is coupled to transmitting means for transmitting a summed output signal over a telephone line, said FM oscillator is at a nominal frequency within a frequency band width of the telephone line on which the signal is being transmitted and said frequency shift key oscillator operating frequencies are distinguishable from the nominal frequency of said FM oscillator but are still within the band width of said telephone line.

* * * * *